US00RE35162E

United States Patent [19]

Draguesku et al.

[11] E Patent Number: Re. 35,162

[45] **Reissued Date of Patent: * Feb. 27, 1996**

[54] RUMEN AND OTHER STOMACH CHAMBER BYPASS NUTRIENTS AND METHODS OF FABRICATION

[76] Inventors: Oliver J. Draguesku, 28582 Jenny La., Menifee Valley, Calif. 92584; Randall A. Johnson, 700 W. Escuda Dr., Glendale, Ariz. 85308

[ * ] Notice: The portion of the term of this patent subsequent to Mar. 3, 2010, has been disclaimed.

[21] Appl. No.: 53,176

[22] Filed: Apr. 26, 1993

Related U.S. Patent Documents

Reissue of:

[64] Patent No.: 5,093,128
Issued: Mar. 3, 1992
Appl. No.: 382,100
Filed: Jul. 18, 1989

[51] Int. Cl.[6] ..... A23K 1/18

[52] U.S. Cl. ..... 424/438; 424/498; 424/468; 424/489; 424/474; 424/458

[58] Field of Search ..... 424/438, 498

[56] References Cited

U.S. PATENT DOCUMENTS

| | | | |
|---|---|---|---|
| 3,037,911 | 6/1962 | Stoyle | 424/147 |
| 3,051,577 | 8/1962 | Babayan et al. | 99/166 |
| 3,089,824 | 5/1963 | Wurster | 424/38 |
| 3,265,629 | 8/1966 | Jensen | 426/218 |
| 3,488,417 | 1/1970 | Krait | 424/489 |
| 3,535,419 | 10/1970 | Siegrist | 424/468 |
| 3,538,215 | 11/1970 | Snyder et al. | 424/38 |
| 3,541,204 | 11/1970 | Sibbald et al. | 424/38 |
| 3,567,818 | 3/1971 | Hemingway | 424/489 |
| 3,655,864 | 4/1972 | Grass et al. | 424/38 |
| 3,696,189 | 10/1972 | Snyder | 424/38 |
| 3,726,805 | 4/1973 | Maekawa et al. | 424/38 |
| 3,959,493 | 5/1976 | Baalsrud | 424/498 |
| 4,177,255 | 12/1979 | Dannelly | 424/489 |
| 4,181,709 | 1/1980 | Dannelly | 424/489 |
| 4,199,561 | 4/1980 | Roth | 424/489 |
| 4,707,361 | 11/1987 | Gustafson | 424/474 |
| 4,800,084 | 1/1989 | Zerbe | 424/474 |
| 4,808,413 | 2/1989 | Joshi | 424/458 |
| 4,842,863 | 6/1989 | Nishimura et al. | 424/438 |
| 4,871,544 | 10/1989 | Eckenhoff | 424/468 |
| 4,876,097 | 10/1989 | Autant et al. | 424/438 |
| 4,877,621 | 10/1989 | Ardaillon et al. | 424/438 |
| 4,935,247 | 6/1990 | Marttila et al. | 424/498 |
| 5,013,569 | 5/1991 | Rubin | 426/585 |
| 5,093,128 | 3/1992 | Draguesku et al. | 424/438 |

*Primary Examiner*—Thurman K. Page
*Assistant Examiner*—William E. Benston, Jr.
*Attorney, Agent, or Firm*—Thomas A. Turner, Jr.

[57] ABSTRACT

A stomach chamber bypass nutrient comprises a beadlet fabricated in two steps having two regions, a first region having the desired nutrient and a second region including fats and calcium based compounds. The nutrient includes lysine, methionine, [tryptothane] *tryptophane*, protein [harmones] *hormones*, vitamins and other nutrients in amounts of from 36% to 59%. The nutrient is fabricated by forming in a first step the nutrient in a beadlet form, and in a second step coating the nutrient beadlet with the second region.

14 Claims, 1 Drawing Sheet

RUMEN AND OTHER STOMACH CHAMBER BYPASS NUTRIENTS AND METHODS OF FABRICATION

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to the art of stomach chamber bypass nutrients useful with certain animals, and more particularly to coated nutrients wherein the coating assists in ypassing certain stomachs in the animal.

2. Description of the Prior Art

In the past, rumen bypass products have been known which require [either very high concentrations of active ingredients or] substantially low concentrations [thereof] *of active ingredients* assembled primarily in a mixture for bypassing the rumen stomach in, for example, cattle. [Loss of certain amounts of the nutrient apparently is expected in such products, but the mixture contains certain elements and compounds which are designed to speed the progress of the overall product through the rumen so that the bulk of the product is supposed to be digested in the stomach chamber or compartment beyond the rumen. In order for such ruminants to succeed, substantially high concentrations of the active ingredient is required. See, for example, United States Letters Patent, No. 3,959,493 to Baalsrud where a minimum of 60% of the bypass product is said to be necessary.] *See, for example, United States Letters Patent, No. 3,959,493 to Baalsrud, et al. where a minimum of 60% of the total product is comprised of a composition selected to frustrate digestion of the remaining less than 40% of the product in the rumen of the cow's stomach. The portion of the product comprising less than 40% comprises the active or nutritional ingredient.*

Some teachings have suggested having 30% or less of various acidic active ingredients, but do not suggest such a composition for rumen bypass. See, for examples, United States Letters Patent, No. 3,696,189 to Snyder; No. 3,726, 805 to Maekawa; and, No. 3,458,625 to Ensor. [For an effective rumen bypass, presumably, as taught by Baalsrud, et al., a higher amount of the active ingredient, on the order of more than 60% would have to be used.]

In the past, it has been known, further, to prepare rumen bypass products by starting with the active ingredient, such as methionine and mixing with it stearic acids and palmitic acids to result in a mixture product, sometimes in a pill or beadlet form. In such a fabrication, some of the active ingredient will be found on or near the surface such that some of the active ingredient will be absorbed or digested within the rumen chamber as the beadlet travels through the stomach chambers of the ruminant.

Such [high concentrations] *arrangements* of the active ingredient are relatively expensive as well as inefficient in that substantial portions of the rumen bypass product actually do not bypass the rumen. It is desired, therefore, to provide a rumen bypass product that is more efficient [, requiring less concentrations of the active ingredient while achieving the same or substantially similar results in animal nutrition]. It is also desired to provide a simple but competent method of preparing such a rumen bypass product.

SUMMARY

In brief, in accordance with one aspect of the present invention, a prepared nutrient is designed to remain substantially undigested by at least the first two stomach chambers, that is the rumen and reticulum of a ruminant but will be digested by a later stomach chamber. The nutrient product includes a first portion consisting of a core which is comprised of beneficial nutrients for which it is desired to be dissolved or digested in a later stomach chamber such as the omasum or abomasum stomach chambers and the intestine. Such beneficial nutrients include amino acids, such as lysine, methionine and tryptophane; hormones such as bovine-somatotrophin, progesterone and growth hormones; minerals such trace minerals selenium, copper, zinc, manganese, cobalt, magnesium and chromium; antibiotics such as teramycin, tetracycline and bacitracin; and, vitamins such as choline, alpha tocopherol, vitamins B, C and D; peptides, fats, enzymes, micro-organisms and medicaments in general.

The nutrient product includes a second portion consisting of a coating to surround and protect the core. The second portion will reduce and substantially prevent digestion of the core within the rumen chamber of the ruminant's stomach. The second portion is formed to coat the core, and is comprised of at least one fatty acid including stearic acids or palmitic acids or both in amounts of [from 36% to 59% ] *from 36% to 59%* by weight of the total weight of the nutrient product. The coating may also include calcium phosphate. The fatty acid of the coating may also include oleic acid and linoleic acid.

The nutrient product is fabricated so that it has a small size in order to put the nutrient product in a liquid feed to the ruminant. The size of the bypass product is from a half millimeter to two millimeters in diameter, with the core being from approximately one-fourth to one millimeter in diameter.

A method for fabricating such small a sized nutrient product in the form of small beadlets is described wherein a methyl cellulose beadlet is used as a starter bead. The methyl cellulose beadlet is deposited or placed in a rotating mill where the beadlet starter is agitated by rotation and air turbulence. Methionine or other nutrients as may be selected are placed in powder or liquid form in the mill and coats the starter beadlet to form a core. The cores are then transported by conduit to another mill to a predetermined coating.

DESCRIPTION OF THE PREFERRED EMBODIMENTS

Figure 1:
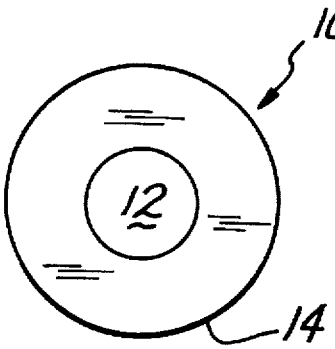
FIG. 1 is a cross-sectional view of a beadlet of the preferred embodiment of the present invention; [and]

A nutrient product 10, reference being had initially to FIG. 1 of the accompanying drawings, for ruminants comprises a first portion which is a core 12 containing the pre-selected nutrients which are desired to be fed to the ruminant. The core 12 is surrounded by a second portion 14 of the product 10. The second portion comprises, in effect, a layer coating the core 12.

The ingredients of the core 12 are pre-selected in order to provide predetermined nutrients or medicaments to the ruminant. Such ingredients include amino acids, hormones, minerals, antibiotics and vitamins. Amino acids which are considered to be effectively fed to the proper stomach of the ruminant through this product are lysine, methionine and tryptophane. It has been found that lysine may be substituted for the methionine, or may be used cumulatively with the methionine. Hormones which have been used effectively include protein harmones, such as, for example, bovine-somatotrophin and growth hormones generally. Effective antibiotics include teramycin, tetracycline, penicillin and bacitracin.

Vitamins which have been used effectively in the product 10 include vitamins B, C and D, choline and alpha tocopherol. Effective minerals include selenium, copper, zinc, manganese, cobalt, magnesium and chromium. Other nutrients as well as beneficial ingredients which may be effectively formed in the core 12 of the present product 10 are peptides, fats, enzymes, microorganisms, as well as medicaments generally.

The coating layer 14 is formed or fabricated of ingredients which will prevent digestion within the rumen or reticulum of a ruminant. The layer 14 is comprised in the present invention of at least one fatty acid, such as stearic acid, palmitic acid or a combination of them. The palmitic acid, C16-H32-O2, comprises at least 20% weight per volume ("w/v"). The stearic acid, C18-H36-O2, is normally included in the range of from 10% to 80% w/v. The coating layer 14 may also include calcium phosphates, CaPO4, which may be monocalcium phosphate or di-calcium phosphate or a combination of both. The fatty acid may further include oleic acid and linoleic acid in such amounts as may be desired.

While the entire and complete set of reactions is not fully understood, it is believed that fat in the amount of from approximately 2% w/v to approximately 6% w/v tends to inhibit digestion of hays and cellulose forages. Further, it is believed that calcium added to the fat in the coating 14 tends to result in better results. It is believed that the coating 14 is attacked by the bile and pancreatic juices resulting in diglycerides, triglycerides and free fatty acids. Further, the stearic acid is dissolved primarily by bile salts and pancreatic juices, which are not normally found in the rumen, thus further insulating the core 12 from attack in the rumen.

The product 10 should be fabricated in the form of beadlets having a size in the range of from one-half millimeter to two millimeters in diameter. Throughout this specification, sizes may be given in distances stated as being of the diameter. However, such forms as beadlets formed in many techniques, including the techniques explained in this specification hereinbelow, will produce small product which frequently is not perfectly spherical in shape, but which is approximately spherical, and "diameter" shall be used herein in this specification to mean the approximation of the distance from one point on the beadlet's surface through the beadlet's center to a surface point on the opposite side of the beadlet.

The relatively small size will be beneficial when mixing the product with a liquid for a liquid feed of the ruminant. Such small sized beadlets 10 can be mixed well with an even distribution throughout a liquid and the liquid can be fed into the ruminant in a known manner. In such a small sized beadlet, it has been found beneficial to maintain the size of the core 12 from approximately one-fourth millimeter to approximately one millimeter in diameter. If the beadlets are too small, however, the beadlets will tend to melt and coagulate together.

The specific gravity of the beadlets 10 should be approximately from about 0.8 to about 1.2. If the beadlets 10 have a weight substantially greater than 1.0, the beadlets 10 may sink or flow too fast through the chambers of the ruminant's stomachs, and substantially defeat the efforts to have digestion take place in a selected stomach chamber. On the other hand, if the beadlets 10 are too light relatively, the beadlets 10 will tend to rise within the fluids in the stomach chambers and tend to plug the stomach's passages.

This embodiment of the present invention can be better understood by reference to the following illustrative example.

EXAMPLE I

A quantity of beadlets fabricated in accordance with the present invention had a size variation of from approximately one millimeter to approximately two millimeters in diameter and were placed in the rumen of a ruminant in an in vivo experiment. The specific gravity of the beadlets 10 was approximately 1.0. In particular, a nylon bag was positioned in situ within the stomach in the rumen. The nylon bag contained beadlets of the present invention and regular feed in substantially equal amounts by weight. The nylon bag was porous to the digestive juices within the rumen. The beadlets comprised in the coating layer 14, 2.5% w/v myristic acid (C14-H28-O2), 0.5% w/v pentedeconoic acid (C15-H30-O2), 50% w/v palmitic acid (C17-H32-O2), 2% w/v margaric acid (C17-H34-O2), 35% w/v stearic acid (C18-H36-)O2), 9% w/v oleic acid (C18-H34-O2), 1% w/v linoleic acid (C18-H32-O2), and from 2% to 5% w/v calcium phosphate. The core 12 consisted of approximately 95% w/v methionine, the remainder being a basically inert methyl cellulose as a starter. Overall, the core weight comprised approximately 52% by weight of the total beadlet.

After 72 hours, the nylon bag was found to have approximately 92% to 94% of the original core nutrient remaining. Approximately 20% of the regular feed was found to be missing, indicating digestion. The beadlets remaining in the nylon bag had the same general shape and size consistency of the beadlets 10 initially placed in the nylon bag in the rumen, i.e. the beadlets 10 showed no or inperceptible degradation in size or content.

EXAMPLE II

The procedure as set forth in Example I above was replicated two additional times. The results were generally similar to those found and reported in Example I.

EXAMPLE III

Four (4) sheep were fed a diet of the beadlets fabricated in accordance with the present invention. The beadlets had a size between ten mesh and fourteen mesh screen size. Each sheep was fed fifty (50) grams of the beadlets for each of four (4) consecutive days. The beadlets comprised in the core approximately 95% w/v methionine with the remainder being a basically inert methyl cellulose binder. The coating layer comprised 2.5% w/v myristic acid (C14-H28-O2), 0.5% w/v pentadeconoic acid (C15-H30-O2), 50% w/v palmitic acid (C16-H32-O2), 2% w/v margaric acid (C17-H 34-O2), 35% w/v stearic acid (C18-H36-O2), 9% w/v oleic acid (C18-H34-O2), 1% w/v linoleic acid (C18-H32-O2), and from 2% to 5% w/v calcium phosphate. Overall, the core weight comprised approximately 52% by weight of the total beadlet.

At the end of the four day period, the digestive system and track of each sheep was examined. In particular, the amount and size of the beadlets in the rumen were compared with the amount and size of the beadlets, if any, in the abomasum, small intestine and colon. The quantity of the beadlets in the colon was observed visually to be less than the quantity in the rumen. However, the quantity of the beadlets appeared visually to be the same, that is to say, evenly divided in the rumen, reticulum, omasum and abomasum. The beadlets in the small intestine and large intestine exhibited digestive deterioration. It appeared, therefore, that the beadlets were not broken down or digested in the rumen, reticulum, omasum or abomasum, but were digested beginning in the small intestine and, generally, during or before the colon in the digestive system.

EXAMPLE IV

A study was conducted using 198 Jersey milk cows to determine the fat output of cows being fed the beadlets of the present invention. Specifically, 109 of the cows were maintained on a normal diet, while 89 of the cows had their diets supplemented with 50 grams daily of the beadlets having a composition in the core of approximately 72.6% w/v methionine with the remainder being a basically inert methyl cellulose starter. The coating layer of the beadlets comprised 2.5% w/v myristic acid (C14-H28-O2), 0.5% w/v pentadeconoic acid (C15-H30-O2), 50% w/v palmitic acid (C16-H32-O2), 2% w/v margaric acid (C17-H34-O2), 35% w/v stearic acid (C18-H36-O2), 9% w/v oleic acid (C18-H34-O2), 1% w/v linoleic acid (C18-H32O2), and from 2 to 5% w/v calcium phosphate. The weights of the core and of the coating were approximately equal.

The study was conducted for four (4) months, and the results were tabulated and averaged on a per cow, per day basis. The results are tabulated in Table I below where the second column lists the daily average of milk in pounds, and the third column lists the percentage of fat in the milk received from cows fed the normal diet, and where the fourth and fifth columns list the corresponding daily average weight in pounds of milk and percentage of fat received from the cows fed the diet supplemented with the beadlets of the present invention:

TABLE I

| | Normal Diet | | Diet Using Beadlets | |
|---|---|---|---|---|
| Month | Mile (lbs.) | % Fat | Milk (lbs.) | % Fat |
| 1st | 37.85 | 3.97 | 41.90 | 4.36 |
| 2nd | 47.00 | 4.25 | 48.91 | 4.31 |
| 3rd | 40.44 | 5.39 | 47.73 | 4.97 |
| 4th | 42.93 | 5.12 | 49.48 | 5.23 |

A fat corrected milk volume (FCMV) can be calculated from these findings. The fat corrected milk volume for the cows maintained on a normal diet (second column below) is compared with the fat corrected milk volume for the cows whose diet was supplemented with the beadlets of the present invention (third column below), and the increase shown (fourth column below). The comparison is given for each month (first column below) in Table II:

TABLE II

| Month | Normal Diet FCMV (lbs.) | Suppl. Diet FCMV (lbs.) | Increase in Lbs./Day |
|---|---|---|---|
| 1st | 42.89 | 52.25 | 9.35 |
| 2nd | 57.04 | 60.24 | 3.20 |
| 3rd | 62.29 | 67.79 | 5.51 |
| 4th | 62.85 | 73.88 | 11.04 |

Figure 2:
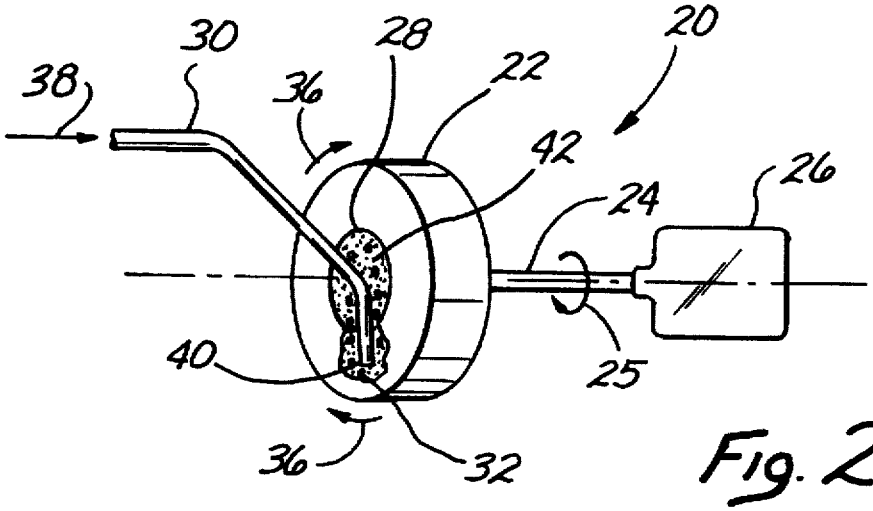
FIG. 2 is a cross-sectional view of a side elevation of the tower and method of fabricating the nutrient according to the preferred embodiment of the present invention; *and,*
Figure 3:
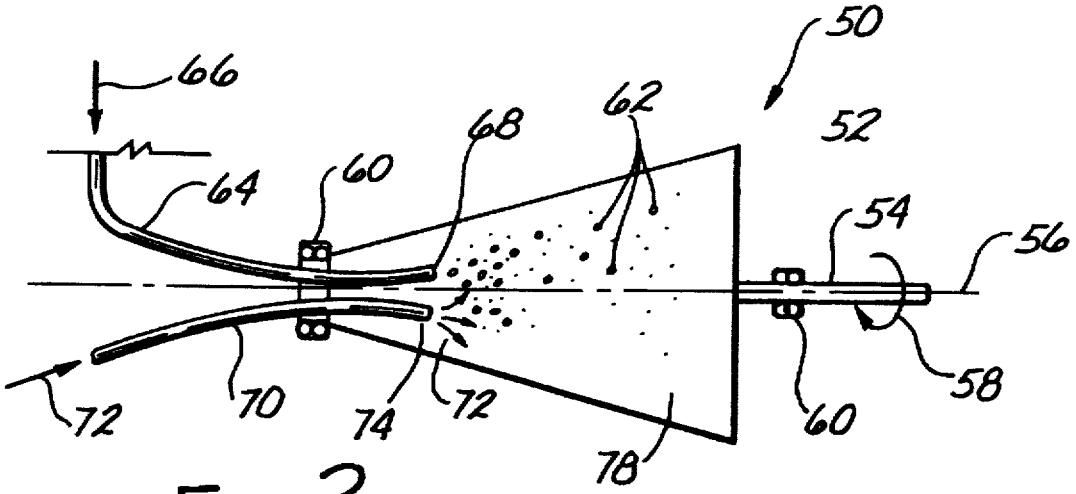
FIG. 3 is a cross-sectional view of a second mill for coating cores of beadlets according to the preferred embodiment of the present invention.

The beadlets 10 are fabricated, reference being had to FIGS. 2 and 3 of the accompanying drawings, in a mill 20. A drum 22 is rotatable about an axle 24 in the direction of arrow 25 by means of a motor 26. The drum 22 has a coaxial opening 28 on one face through which a hose or conduit 30 is inserted.

Starter beadlets 32 made of methyl cellulose are placed within the drum 22. The starter beadlets 32 have a size of approximately from 60 to 40 mesh screen size. The atomssphere within the drum 22 is comprised of methionine 42 in powder form. The starter beadlets 32 and the powdered methionine 42 are agitated by rotation of the drum 22 axially in the direction of arrows 36.

Agitation of the material within the drum 22 is increased by forcing air at approximately 100 degrees Fahrenheit through the conduit 30 in the direction of arrow 38. The forced air at the elevated temperature exits through the end of the conduit 40 to stir the starter beadlets 32 and the powdered methionine 42 within the drum 22 to expose as much of the starter beadlets 32 to the coating action of the methionine 42 to form cores of methionine. When the cores have reached a size of approximately from 30 to 20 mesh screen size, they are removed from the drum and tansported to a second mill for coating, as will be explained below. In alternative embodiments, other compositions for the core can be accomplished by inserting the composition desired within the drum 22. The methionine as shown, or any other composition may be inserted in powder form or may be inserted in liquid form. The selection should be made according to which form is better suited for the composition selected, and which form more readily results in the desired core size and density.

In FIG. 3, a second mill 50 is shown having drum 52. Drum 52 is shown rotatable on axle 52 about centerline 56 in the direction of arrow 58 from a source of rotary power, not shown. The drum 52 is held in a rotating position by mounting it on roller bearings mounts 60.

The cores 62 formed in the first mill 20 are directed by conduit 64 in the direction of arrow 66 to the interior of the drum 52. The cores are forced through the opening 68. The composition selected for coating the cores 62 is prepared in a liquified form and transmitted through conduit 70 in the direction of arrow 72 under pressure. The liquified composition is forced through nozzle 74 inside the interior of the drum 52, as indicated by the arrows 72. The liquid composition 78 disperses within the drum 52 and coats the cores 62 to form beadlets 10. The interior of the drum 52 is kept at a temperature of approximately 100 degrees Fahrenheit, and the liquid evaporates to leave the beadlet 10 as a distinct beadlet. The liquid composition 78 and the cores 62 are agitated within the interior of the drum 52 by rotating the drum 52 about its axle 54, and by the force of the liquid through the nozzle 74 and the force of the cores 62 through the opening 68. When the beadlets having a coating thereon build up to a size of approximately from 20 to 10 mesh screen size, they are removed from the drum 52.

The coating composition 78 adheres to the cores 62 to form the desired beadlet 10 of the present invention. Size selection is made by removing the beadlets 10 at a time when the coating process accomplishes the desired diameter or screen size.

The foregoing detailed description of my invention and of preferred embodiments as to products, compositions and processes, is illustrative of specific embodiments only. It is to be understood, however, that additional embodiments may be perceived by those skilled in the art. The embodiments described herein, together with those additional embodiments, are considered to be within the scope of the present invention.

I claim:

1. A stomach chamber by-pass beadlet comprising:

a. first core portion being in an amount of [from 36% to 59%] *more than 40%* by weight of the total weight of said by-pass beadlet comprising at least one active ingredient digestible in a stomach chamber and selected from the group consisting of animo acids, fats, peptides, hormones, medicaments, vitamins, microorganisms, minerals, enzymes and combinations thereof; and, b. a second coating portion substantially surrounding and coating said first core portion and which is substantially indigestible in a first ruminant stomach chamber but substantially digestible in a stomach chamber and intestines after said first stomach chamber comprising at least one fatty acid selected from the group consisting of stearic acid, palmitic acid and combinations thereof.

2. The beadlet of claim 1 wherein said nutrient is in the form of a beadlet having the size of from approximately one-half millimeter diameter to approximately two millimeters diameter.

3. The beadlet of claim 1 wherein said second portion further comprises at least one calcium phosphate.

4. The beadlet of claim 3 wherein said calcium phosphate is present in an amount of from 0.1% to 5% by weight of the total weight of the by-pass nutrient.

5. The beadlet of claim 1 wherein said fatty acid of said second portion comprises at least 20% by weight palmitic acid.

6. The beadlet of claim 5 wherein said fatty acid further comprises approximately from 10% to 80% by weight stearic acid.

7. The beadlet of claim 5 wherein said fatty acid further comprises approximately from 10% to 60% by weight oleic acid and linoleic acid.

8. The beadlet of claim 1 wherein said first portion comprises from 40% to [60% 173 *59%* by weight of said by-pass nutrient.

9. The beadlet of claim 8 further comprising in said first core portion an inert starter, and wherein the said at least one active ingredient digestible in a stomach chamber comprises from 60% to 98% by weight of said first core portion.

10. The beadlet of claim 1 wherein said animo acids are selected from the group consisting of lysine, methionine, tryptophane and combinations thereof.

11. The beadlet of claim 1 wherein said hormones are selected from the group selected from the group consisting of [bovine-somatotrophin] *bovine-somatotropin*, progesterone and growth hormones.

12. A stomach chamber by-pass beadlet having a coated core, the core of said beadlet having an approximately beadlet shape and comprising at least one material digestible in a stomach chamber and selected from the group consisting of animo acids, fats, peptides, hormones, medicaments, vitamins, micro-organisms, minerals, enzymes and combinations thereof in an amount [from 36% to 59%] *from 40% to 59%* by weight of the by-pass beadlet, said core having a coating substantially surrounding said core, said coating being substantially indigestible *in* in a first ruminant stomach chamber but substantially digestible in a later stomach chamber and intestines, said coating comprising at least one fatty acid selected from the group consisting of stearic acid and palmitic *acid* and combinations thereof, said beadlet having a specific gravity of approximately from 0.8 to 1.2.

13. A stomach chamber by-pass beadlet having a coated core comprising:

a. the core of said beadlet having an approximately beadlet shape and comprising at least one material digestible in a stomach chamber and selected from the group consisting of animo acids, fats, peptides, hormones, medicaments, vitamins, micro-organisms, minerals, enzymes and combinations thereof in an amount of [from 36% to 59%] *more than 40%* by weight of the by-pass beadlet; and, b. said core having a coating substantially surrounding said core, said coating being substantially indigestible in a first stomach chamber but substantially digestible in a later stomach chamber and intestines, said coating comprising at least one fatty acid selected from the group consisting of stearic acid and palmitic acid and combinations thereof, said beadlet having a diameter of approximately from one-half to two millimeters.

14. The beadlet of claim 12 wherein said beadlet has a specific gravity of approximately one.

* * * * *